United States Patent
Dietz

(10) Patent No.: US 7,148,260 B2
(45) Date of Patent: Dec. 12, 2006

(54) WATER-BASED EMULSIFIER WAX GELS INCLUDING FREE SPHINGOID BASES AND OIL IN-WATER EMULSION INCLUDING THE SAME

(75) Inventor: Thomas Dietz, Glen Allen, VA (US)

(73) Assignee: Goldschmidt GmbH, Essen (DE)

( * ) Notice: Subject to any disclaimer, the term of this patent is extended or adjusted under 35 U.S.C. 154(b) by 326 days.

(21) Appl. No.: 10/724,379

(22) Filed: Nov. 28, 2003

(65) Prior Publication Data

US 2004/0110851 A1  Jun. 10, 2004

(30) Foreign Application Priority Data

Nov. 28, 2002  (DE)  ................................ 102 55 554

(51) Int. Cl.
- B01J 13/00 (2006.01)
- C08J 3/02 (2006.01)
- A61K 38/00 (2006.01)
- A61K 9/10 (2006.01)

(52) U.S. Cl. ...................... 516/108; 516/926; 516/928; 424/450; 514/2; 514/579; 536/53

(58) Field of Classification Search ................. 516/108
See application file for complete search history.

(56) References Cited

U.S. PATENT DOCUMENTS

| 5,264,567 A * | 11/1993 | Numata et al. ................ 536/53 |
| 5,665,778 A * | 9/1997 | Semeria et al. ............. 514/613 |
| 6,015,574 A * | 1/2000 | Cannell et al. ............. 424/450 |
| 6,248,352 B1 * | 6/2001 | Semeria et al. ............. 424/450 |
| 6,362,142 B1 * | 3/2002 | Weber et al. ................ 510/119 |
| 2002/0010215 A1 * | 1/2002 | Shiroyama et al. ......... 514/625 |

FOREIGN PATENT DOCUMENTS

| JP | 07165690 A * | 6/1995 |
| WO | WO 98/53797 | 12/1998 |
| WO | WO 99/29293 | 6/1999 |
| WO | WO 00/53568 | 9/2000 |

\* cited by examiner

*Primary Examiner*—Randy Gulakowski
*Assistant Examiner*—Timothy J. Kugel
(74) *Attorney, Agent, or Firm*—Scully, Scott, Murphy & Presser, P.C.

(57) ABSTRACT

Water-based emulsifier wax gels are provided that include skin-identical sphingolipids The present invention also provides a process for the preparation of such gels, the use of such gels for the preparation of oil-in-water emulsions, and the resulting emulsions that contain the inventive gels.

11 Claims, No Drawings

WATER-BASED EMULSIFIER WAX GELS INCLUDING FREE SPHINGOID BASES AND OIL IN-WATER EMULSION INCLUDING THE SAME

FIELD OF THE INVENTION

The present invention relates to water-based emulsifier wax gels comprising skin-identical sphingolipids, as well as a process for their preparation, their use for the preparation of oil-in-water emulsions, and to the resulting emulsions.

BACKGROUND OF THE INVENTION

For some time, skin-identical lipids such as ceramides and phytosphingosines have been commercially available for use in cosmetic products. Ceramides and phytosphingosines are high-melting, crystalline substances with only low solubility in cosmetic oils, which considerably impair their incorporation and stabilization in end products. Thus, for example, an oil phase that comprises 0.2% phytosphingosine must be heated to more than 90° C. so that the phytosphingosine is completely dissolved. However, a heating temperature of 90° C. represents a problem for many production plants since this temperature cannot be reached. A further problem that may arise is that during the homogenization in the preparation of an oil-in-water emulsion inversion to an unusable, inhomogeneous water-in-oil emulsion takes place when phytosphingosine is in the oil phase. This phenomenon is observed in particular with more hydrophobic O/W emulsifiers, the so-called lipid emulsifiers.

WO-A-00/53568 describes sphingoid based derivatives and the use thereof. In particular, the '568 reference describes salts which have an essentially improved solubility in an aqueous environment and thus improved efficiency in topical applications. However, due to their electrolyte character, such salts represent a particular emulsion loading and have incompatibility with stabilizers of the hydrocolloid type, such as, for example, carbomer or xanthan gum.

WO-A-99/29293 describes compositions that comprise a combination of a free sphingoid base and a ceramide. The compositions are suitable for application to the human skin and have barrier functions, particularly in the case of skin conditions that are burdened with unordered deregulation of cell growth or of differentiation of inflammation or of an infectious stage. For example, oil-in-water emulsions are described herein which comprise defined emulsifiers. These are said to be suitable for forming a lamellar phase (liquid crystalline or gel phase). The lamellar phases are formed at the oil-water interface of an oil-in-water emulsion and comprise directly the free sphingoid base and the ceramide.

WO-A-98/53797 relates to encapsulated, water-insoluble active ingredients having an amphiphilic character with a content of water and at least one surfactant selected from the group of esters of long-chain carboxylic acids with carboxylic acids containing hydroxyl groups, or salts thereof and the esters of long-chain carboxylic acids with polyalcohols. Such active ingredients are used in the preparation of pharmaceutical, agrochemical or cosmetic formulations. Without more specific working examples, the active ingredients mentioned in the text of the '797 reference are also ceramides, lipophilic amides from a saturated and unsaturated aminodiol radical (diphytosphingosines and sphingosines) and saturated aminotriol radical (phytosphingosines), long-chain fatty acid radicals and long-chain alkyl radicals in the aminodiol moiety. The active ingredient is heated together with the surfactant to 80° C. with stirring and mixed at 75° to 80° C. until a completely clear solution is obtained. After cooling to 25° C. (room temperature), the mixture is heated to about 40° C., water is added and intensive stirring is carried out until the system is completely homogenized.

It is an object of the present invention to provide a way of incorporating skin-identical lipids such as ceramides and phytosphingosine into oil-in-water emulsions which solves the above-described problems of the prior art.

SUMMARY OF THE INVENTION

The object specified above is achieved according to the present invention in a first embodiment by providing water-based emulsifier wax gels which comprise
   a) skin-identical sphingolipids,
   b) at least one emulsifier,
   c) at least one wax-like consistency-imparting agent,
   d) water, and
   e) optionally further auxiliaries.

It has surprisingly been found by the present applicant that skin-identical lipids, in particular ceramides and phytosphingosine, can be stably incorporated into an aqueous emulsifier wax gel. The inventive gel can then, in turn, be used as a carrier to introduce the lipid into an oil-in-water emulsion by adding the gel to the water phase prior to emulsification. It has also been found that emulsions in which the lipid has been incorporated in this manner have different physical properties, such as, for example, viscosity, than those emulsions in which the lipid has been incorporated via the oil phase, although both emulsions have identical material compositions. In addition, it has been found that emulsions that cannot be prepared by adding the lipid to the oil phase can, however, be prepared by adding the lipid to the water phase via an emulsifier wax gel.

DETAILED DESCRIPTION OF THE INVENTION

For the purposes of the present invention, the sphingolipids are preferably chosen from ceramides, as are defined in WO-A-99/29293, in particular in a form that corresponds, in the stereochemical configuration, to a ceramide which is obtained from mammal skin and/or from free sphingoid bases, in particular sphingosine, sphinganine and/or phytosphingosine and/or 6-hydroxy-4-sphingenine.

Although the amount of the sphingolipids in the emulsifier wax gels according to the present invention can vary within a wide range, it is particularly preferred for the purposes of the present invention if the gels comprise sphingolipids in an amount from 1 to 4% by weight.

The water-based emulsifier wax gels according to the present invention comprise at least one or, in some instances, two or more emulsifiers. Additionally, nonionic and anionic emulsifiers, which are particularly preferred, cationic or zwitterionic emulsifiers may also be used.

In a preferred embodiment of the present invention, the emulsifier is chosen from fatty acids and neutralized fatty acids; glyceryl mono-fatty acid esters, ethoxylated fatty alcohols and/or esters; fatty alcohols with a high degree of ethoxylation and/or fatty alcohols with a low degree of ethoxylation, polyglycerol esters, sugar esters, lecithins and/or phospholipids.

Suitable emulsifiers are, for example, nonionogenic or anionic surfactants selected from at least one of the following groups:

addition products of from 2 to 30 mol of ethylene oxide and/or 0 to 5 mol of propylene oxide onto linear fatty alcohols having 8 to 22 carbon atoms, onto fatty acids having 12 to 22 carbon atoms and onto alkylphenols having 8 to 15 carbon atoms in the alkyl group;

$C_{12}$–$C_{18}$ fatty acid mono- and diesters of addition products of from 1 to 30 mol of ethylene oxide onto glycerol;

glycerol mono- and diesters and sorbitan mono- and diesters of saturated and unsaturated fatty acids having 6 to 22 carbon atoms and ethylene oxide addition products thereof;

alkyl mono- and oligoglycosides having 8 to 22 carbon atoms in the alkyl radical and ethoxylated analogs thereof;

addition products of 15 to 60 mol of ethylene oxide onto castor oil and/or hydrogenated castor oil; and polyol, and in particular polyglycerol, esters, such as, for example, polyglycerol polyricinoleate, polyglycerol 12-hydroxystearate or polyglycerol dimerate.

Likewise suitable are mixtures of compounds from two or more of these classes of substance;

addition products of from 2 to 15 mol of ethylene oxide onto castor oil and/or hydrogenated castor oil;

partial esters based on linear, branched, unsaturated or saturated fatty acids having from 6 to 22 carbon atoms, ricinoleic acid, and 12-hydroxystearic acid and glycerol, polyglycerol, pentaerythritol, dipentaerythritol, sugar alcohols (for example, sorbitol), alkyl glucosides (for example, -methyl glucoside, butyl glucoside, or lauryl glucoside), and polyglucosides (for example, cellulose);

mono-, di- and triallcyl phosphates, and mono-, di- and/or tn-PEG alkyl phosphates;

wool wax alcohols;

polysiloxane-polyether copolymers and corresponding derivatives;

mixed esters of pentaerythritol, fatty acids, citric acid and fatty alcohol according to DE-B-11 65 574 and/or mixed esters of fatty acids having 6 to 22 carbon atoms, methylglucose and polyols, preferably glycerol or polyglycerol, and polyalkylene glycols.

Likewise suitable are mixtures of compounds from two or more of these classes of substance;

addition products of from 2 to 15 mol of ethylene oxide onto castor oil and/or hydrogenated castor oil;

partial esters based on linear, branched, unsaturated or saturated $C_{6/22}$-fatty acids, ricinoleic acid, and 12-hydroxystearic acid and glycerol, polyglycerol, pentaerythritol, dipentaerythritol, sugar alcohols (for example, sorbitol), alkyl glucosides (for example, —methyl glucoside, butyl glucoside, or lauryl glucoside), and polyglucosides (for example, cellulose);

mono-, di- and trialkyl phosphates, and mono-, di- and/or tri-PEG alkyl phosphates;

wool wax alcohols;

polysiloxane-polyether copolymers and corresponding derivatives;

mixed esters of pentaerythritol, fatty acids, citric acid and fatty alcohol according to DE-B-11 65 574 and/or mixed esters of fatty acids having 6 to 22 carbon atoms, methylglucose and polyols, preferably glycerol or polyglycerol, and polyalkylene glycols.

The addition products of ethylene oxide and/or propylene oxide onto fatty alcohols, fatty acids, alkylphenols, glycerol mono- and diesters, and sorbitan mono- and diesters of fatty acids or onto castor oil are known, commercially available products. These are homolog mixtures whose average degree of alkoxylation corresponds to the ratio of the material amounts of ethylene oxide and/or propylene oxide and substrate with which the addition reaction is carried out.

In addition, zwitterionic surfactants may be used as emulsifiers. Zwitterionic surfactants refer to those surface-active compounds which carry at least one quaternary ammonium group and at least one carboxylate or one sulfonate group in the molecule. Particularly suitable zwitterionic surfactants are the so-called betaines, such as N-alkyl-N,N-dimethylammonium glycinates, for example, cocoalkyldimethylammonium glycinate, N-acylaminopropyl-N,N-dimethylammonium glycinates, for example cocoacylaminopropyldimethylammonium glycinate, and 2-alkyl-3-carboxymethyl-3-hydroxyethylimidazolines having, in each case, 8 to 18 carbon atoms in the alkyl or acyl group, and also cocoacylaminoethylhydroxyethyl carboxymethylglycinate.

Particular preference is given to the fatty acid amide derivative known under the Cosmetic, Toiletry and Fragrance Association (CTFA) name Cocamidopropyl Betaine. Likewise suitable emulsifiers are ampholytic surfactants. Ampholytic surfactants are understood as meaning those surface-active compounds which, apart from a $C_8$–$C_{18}$ alkyl or -acyl group in the molecule, contain at least one free amino group and at least one —COOH or —$SO_3$H group and are capable of forming internal salts. Examples of suitable ampholytic surfactants include, but are not limited to: N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids having, in each case, about 8 to 18 carbon atoms in the alkyl group. Particularly preferred ampholytic surfactants are N-cocoalkylaminopropionate, cocoacylaminoethylaminopropionate and $C_{12/18}$-acylsarcosine. As well as the ampholytic emulsifiers, quaternary emulsifiers are also suitable; those of the ester quat type, preferably methylquatemized di-fatty acid triethanolamine ester salts, being particularly preferred.

For the purposes of the present invention, the gels according to the invention preferably comprise emulsifiers in an amount from 0.5 to 6.0% by weight.

As well as the sphingolipids, emulsifiers and water, the gels according to the present invention necessarily comprise at least one or, in some cases, two or more consistency-imparting agents.

Suitable consistency-imparting agents are primarily fatty alcohols or hydroxy fatty alcohols having 12 to 22, preferably 16 to 18, carbon atoms and also partial glycerides, fatty acids or hydroxy fatty acids.

The amount of consistency-imparting agent used is essentially governed by the desired viscosity of the gel to be prepared. Accordingly, for the purposes of the present invention, it is particularly preferred if the gels comprise the consistency-imparting agent in an amount from 1 to 8% by weight.

If, for the purposes of the present invention, the use of wax-like consistency-imparting agents is defined, then this is understood as meaning consistency-imparting agents which are kneadable at 20° C., solid to brittly hard, coarse to finely crystalline, transparent to opaque, but not glass-like; melt above 40° C. without decomposition, are of relatively low viscosity and non-thread-drawing at just a little above the melting point, have strongly temperature-dependent consistency and solubility, and can be polished with slight pressure, and which differ from similar synthetic or natural products, for example resins, plastic masses, metal soaps, etc. primarily by virtue of the fact that they usually convert to the melt-liquid, low-viscosity state between 50° and 90° C., in exceptional cases also up to about 200° C., and are virtually free from ash-forming compounds.

The amount of water that may be present in the gels according to the present invention can vary within wide ranges. For the purposes of the present invention, particular preference is given to gels that comprise water in an amount from 80 to 98% by weight.

The gels according to the present invention can optionally comprise additional auxiliaries that are customary in the field of cosmetics or pharmacy. For the purposes of the present invention, particular preference is given to humectants and/or preservatives. Corresponding additional auxiliaries may be present according to the present invention in the gels in an amount from 0.01 to 10.0% by weight.

A further embodiment of the present invention consists in the preparation of the emulsifier wax gels as are defined at the outset. According to this aspect of the present invention, the emulsifier wax gels can be prepared by melting skin-identical sphingolipids with at least one emulsifier, at least one consistency-imparting agent and optionally additional auxiliaries, and, at a temperature which is increased relative to room temperature, bringing the mixture into contact with water, homogenizing it and then cooling it to room temperature with stirring.

The emulsifier wax gels obtainable in this way are particularly suitable for the preparation of oil-in-water emulsions that comprise sphingolipids, in some cases even in high quantitative proportions.

For the purposes of the present invention, the emulsifier wax gel is preferably incorporated into the aqueous phase of the emulsion.

A further embodiment of the present invention relates to oil-in-water emulsions that are obtainable according to the process defined above. Such emulsions comprise sphingolipids, optionally in a very high and thus efficient concentration, for example in an amount of from 0.01 to 0.4% by weight.

The following examples are given to provide an illustration of how the inventive gels are prepared as well as an illustration of using the gels for providing emulsions.

EXAMPLE 1

Emulsifier wax gel containing phytosphingosine:

The components of phase A, see Table 1 below, were heated to 105° to 110° C. until the phytosphingosine was dissolved to give a clear solution. The components of phase B, see Table 1 below, were then heated to 90° C., added to phase A, which was at a temperature of 95° C., and intensively homogenized. The mixture was then cooled to room temperature with moderate stirring.

TABLE 1

| A | Ceteareth-25 | 2.0% |
|---|---|---|
|   | Glyceryl stearate | 2.5% |
|   | Cetearyl alcohol | 3.5% |
|   | Stearic acid | 1.0% |
|   | Phytosphingosine | 2.0% |
| B | Glycerol | 3.0% |
|   | Benzyl alcohol, methylchloroisothiazolinone, methylisothiazolinone | 0.1% |
|   | Water | 85.9% |

COMPARATIVE EXAMPLE 1

Emulsion which cannot be prepared by adding phytosphingosine to the oil phase:

The components of phase A, see Table 2, were heated to 90° C. until the phytosphingosine was completely dissolved. The components of phase B, see Table 2, were heated to 90° C., added to phase A and homogenized. During the homogenization, the initially thin-liquid O/W emulsion changed into a thick-liquid and an inhomogeneous W/O emulsion which could no longer be used was obtained.

TABLE 2

| A | Polyglyceryl-3 methylglucose disteareate | 3.0% |
|---|---|---|
|   | Cetearyl alcohol | 1.75% |
|   | Glyceryl stearate | 0.75% |
|   | Isocetyl palmitate | 5.5% |
|   | Ethylhexyl stearate | 9.0% |
|   | Avocado oil | 3.0% |
|   | Tocopheryl acetate | 1.0% |
|   | Phytosphingosine | 0.2% |
| B | Glycerol | 3.0% |
|   | Allantoin | 0.1% |
|   | Chloroacetamide and sodium benzoate | 0.1% |
|   | Water | 72.6% |

EXAMPLE 2

Emulsion which can be prepared using the aqueous emulsifier wax gel from Example 1.

The components of phase A, see Table 3, were heated to 75° C. The components of phase B, see Table 3, were heated to 75° C., added to phase A and homogenized. The mixture was then cooled to room temperature with moderate stirring. The resulting emulsion had a smooth and brilliant appearance and had very good storage stability.

TABLE 3

| A | Polyglyceryl-3 methylglucose disteareate | 3.0% |
|---|---|---|
|   | Cetearyl alcohol | 1.75% |
|   | Glyceryl stearate | 0.75% |
|   | Isocetyl palmitate | 5.5% |
|   | Ethylhexyl stearate | 9.0% |
|   | Avocado oil | 3.0% |
|   | Tocopheryl acetate | 1.0% |
| B | Glycerol | 3.0% |
|   | Allantoin | 0.1% |
|   | Emulsifier wax gel with phytosphingosine (2%) from Example 1 | 10.0% |
|   | Chloroacetamide and sodium benzoate | 0.1% |
|   | Water | 62.6% |

EXAMPLE 3/COMPARATIVE EXAMPLE 2

Emulsions with identical composition but different physical properties depending on the incorporation of phytosphingosine:

Preparation of Comparative Example 2

The components of phase A, see Table 4, were heated to 90° C. until the phytosphingosine was completely dissolved. The components of phase B, see Table 4, were heated to 90° C., added to phase A and homogenized. The mixture was then cooled to 65° C. with gentle stirring, phase C and D, see Table 4, were added, the mixture was again briefly homogenized and further cooled to room temperature with gentle stirring.

TABLE 4

| | | |
|---|---|---|
| A | Bis-PEG/PPG-16/16 PEG/PPG-16/16 dimethicone (and) caprylic/capric triglyceride | 1.0% |
| | Ceteareth-25 | 1.0% |
| | Glyceryl stearate | 4.0% |
| | Cetearyl alcohol | 1.5% |
| | Stearic acid | 0.5% |
| | Decyl cocoate | 5.3% |
| | Ethylhexyl palmitate | 5.0% |
| | Caprylic/capric triglyceride | 6.5% |
| | Phytosphingosine | 0.2% |
| B | Glycerol | 3.0% |
| | Chloroacetamide (and) sodium benzoate | 0.1% |
| | Water | 70.72% |
| C | Sodium hydroxide | 0.43% |
| D | Carbomer | 0.15% |
| | Ethylhexyl palmitate | 0.6% |

Viscosity (Brookfield, Spindle C, 10 rpm): 70 Pas.

Preparation of Example 3

The components of phase A, see Table 5, were heated to 75° C. The components of phase B, see Table 5, were heated to 75° C., added to phase A and homogenized. The mixture was then cooled to 65° C. with gentle stirring, phase C and D, see Table 5, were added, then the mixture was homogenized again and cooled further to room temperature with gentle stirring.

TABLE 5

| | | |
|---|---|---|
| A | Bis-PEG/PPG-16/16 PEG/PPG-16/16 dimethicone (and) caprylic/capric triglyceride | 1.0% |
| | Ceteareth-25 | 0.8% |
| | Glyceryl stearate | 3.75% |
| | Cetearyl alcohol | 1.15% |
| | Stearic acid | 0.4% |
| | Decyl cocoate | 5.3% |
| | Ethylhexyl palmitate | 5.0% |
| | Caprylic/capric triglyceride | 6.5% |
| B | Glycerol | 2.7% |
| | Chloroacetamide (and) sodium benzoate | 0.1% |
| | Water | 62.12% |
| | Emulsifier wax gel with phytosphingosine (2%) from Example 1 | 10.0% |
| C | Sodium hydroxide | 0.43% |
| D | Carbomer | 0.15% |
| | Ethylhexyl palmitate | 0.6% |

Viscosity (Brookfield, Spindle C, 10 rpm): >100 Pas.

While the present invention has been particularly shown and described with respect to preferred embodiments thereof, it will be understood by those skilled in the art that the foregoing and other changes in forms and details may be made without departing from the scope and spirit of the present invention. It is therefore intended that the present invention not be limited to the exact forms and details described and illustrated, but fall within the scope of the appended claims.

What is claimed is:

1. A water-based emulsifier wax gel comprising:
  a) 1 to 4% by weight of a skin-identical free sphingoid base,
  b) 0.5 to 6.0% by weight of at least one nonionic or anionic emulsifier,
  c) 1 to 8% by weight of at least one wax-like consistency-imparting agent, and
  d) 80 to 98% by weight water.

2. The gel as claimed in claim 1, further comprising additional auxiliaries.

3. The gel as claimed in claim 2, wherein the auxiliaries are chosen from humectants, preservatives and mixtures thereof.

4. The gel as claimed in claim 2, wherein said auxiliaries are present in an amount from 0.1 to 10% by weight.

5. The gel as claimed in claim 1, wherein the skin-identical free sphingoid base is selected from the group consisting of sphingosine, sphinganine, phytosphingosine, and 6-hydroxy-4-sphingenine.

6. The gel as claimed in claim 1, wherein the emulsifier is selected from fatty acids and neutralized fatty acids; glyceryl mono-fatty acid esters, ethoxylated fatty alcohols and/or esters; fatty alcohols with a high degree of ethoxylation and/or fatty alcohols with a low degree of ethoxylation, polyglycerol esters, sugar esters, lecithins, phospholipids and any combination thereof.

7. The gel as claimed in claim 1, wherein the consistency-imparting agent is selected from fatty alcohols or hydroxy fatty alcohols having 12 to 22 carbon atoms, partial glycerides, fatty acids and hydroxy fatty acids.

8. A process for the preparation of emulsifier wax gels comprising melting a skin-identical free sphingoid base with at least one non-ionic or anionic emulsifier, at least one consistency-imparting agent at a temperature which is increased relative to room temperature, bringing the mixture into contact with water, homogenizing the mixture and then cooling the mixture to room temperature with stirring.

9. The process of claim 8 further comprising adding an additional auxiliary to a molten oil phase.

10. An oil-in-water emulsion comprising a water-based emulsifier wax gel which comprises a skin-identical free sphingoid base, at least one nonionic or anionic emulsifier, at least one wax-like consistency-imparting agent, and water.

11. The emulsion as claimed in claim 10, wherein said skin-identical free sphingoid base is present in an amount from 0.01 to 0.4% by weight.

* * * * *